(12) United States Patent
Xu et al.

(10) Patent No.: US 9,669,377 B2
(45) Date of Patent: Jun. 6, 2017

(54) IONIC LIQUID REACTOR WITH HEAT EXCHANGER

(71) Applicant: UOP LLC, Des Plaines, IL (US)

(72) Inventors: Zhanping Xu, Iverness, IL (US); James Hagen, Arlington Heights, IL (US); Sanford A. Victor, Buffalo Grove, IL (US); Phillip F. Daly, Palatine, IL (US); Kurt Detrick, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 3 days.

(21) Appl. No.: 14/755,446

(22) Filed: Jun. 30, 2015

(65) Prior Publication Data

US 2016/0167012 A1 Jun. 16, 2016

Related U.S. Application Data

(60) Provisional application No. 62/090,970, filed on Dec. 12, 2014.

(51) Int. Cl.
*B01J 19/00* (2006.01)
*B01J 19/18* (2006.01)
*B01J 19/24* (2006.01)
*C07C 2/62* (2006.01)
*F28F 9/013* (2006.01)
(Continued)

(52) U.S. Cl.
CPC .......... *B01J 19/006* (2013.01); *B01J 19/1862* (2013.01); *B01J 19/2415* (2013.01); *C07C 2/62* (2013.01); *F28D 7/04* (2013.01); *F28D 7/06* (2013.01); *F28D 7/14* (2013.01); *F28D 7/1646* (2013.01); *F28F 9/0136* (2013.01); *B01J 2219/0009* (2013.01); *B01J 2219/00085* (2013.01); *B01J 2219/00094* (2013.01); *B01J 2219/00103* (2013.01); *B01J 2219/00763* (2013.01); *F28F 2009/226* (2013.01)

(58) Field of Classification Search
CPC ...... B01J 19/00; B01J 19/0053; B01J 19/006; B01J 19/18; B01J 19/1862; B01J 19/24; B01J 19/2415; B01J 2219/00049; B01J 2219/00051; B01J 2219/00074; B01J 2219/00076; B01J 2219/00085; B01J 2219/00087; B01J 2219/0009; B01J 2219/00094; B01J 2219/00103; B01J 2219/00761; B01J 2219/00763
See application file for complete search history.

(56) References Cited

U.S. PATENT DOCUMENTS

| | | |
|---|---|---|
| 3,696,168 A | 10/1972 | Vanderveen |
| 5,785,933 A | 7/1998 | Cunningham et al. |

(Continued)

FOREIGN PATENT DOCUMENTS

WO   WO 2011/015662 A2   2/2011

*Primary Examiner* — Natasha Young (57) ABSTRACT

An ionic liquid reactor unit and a process for controlling heat generation from an ionic liquid reactor unit. The ionic liquid reactor unit may include an external heat exchanger. The effluent from the reactor is separated in a separation zone allowing the hydrocarbon phase to transfer heat to a cooling fluid. The heat exchanger may be a tube-in-shell, a spiral plate heat exchanger, a hair pin heat exchanger. The heat exchanger accommodates the separation of the ionic liquid from the hydrocarbon phase, and may allow for the ion liquid to be drained.

18 Claims, 5 Drawing Sheets

(51) Int. Cl.
   *F28D 7/04*    (2006.01)
   *F28D 7/06*    (2006.01)
   *F28D 7/14*    (2006.01)
   *F28D 7/16*    (2006.01)
   *F28F 9/22*    (2006.01)

(56) References Cited

U.S. PATENT DOCUMENTS

| | | |
|---|---|---|
| 7,432,408 B2 | 10/2008 | Timken et al. |
| 7,727,925 B2 | 6/2010 | Elomari et al. |
| 7,951,889 B2 | 5/2011 | Bergman et al. |
| 8,142,725 B2 | 3/2012 | Hommeltoft et al. |
| 8,163,856 B2 | 4/2012 | Bergman et al. |
| 8,183,425 B2 | 5/2012 | Luo et al. |
| 8,383,874 B2 | 2/2013 | Strauss et al. |
| 8,507,396 B2 | 8/2013 | Elomari et al. |
| 8,524,965 B2 | 9/2013 | Campbell et al. |
| 8,552,243 B2 | 10/2013 | Liu et al. |
| 8,692,048 B2 | 4/2014 | Liu et al. |
| 8,729,329 B2 | 5/2014 | Hommeltoft et al. |
| 2009/0171133 A1 | 7/2009 | Luo et al. |
| 2011/0282114 A1 | 11/2011 | Luo et al. |
| 2011/0319693 A1 | 12/2011 | Hommeltoft et al. |
| 2012/0165593 A1 | 6/2012 | Liu et al. |
| 2013/0004378 A1 | 1/2013 | Luo et al. |
| 2013/0066130 A1 | 3/2013 | Luo et al. |
| 2013/0066132 A1* | 3/2013 | Cleverdon .......... B01J 31/0284 585/719 |
| 2013/0066133 A1 | 3/2013 | Cleverdon et al. |
| 2013/0331625 A1 | 12/2013 | Liu et al. |
| 2014/0066678 A1 | 3/2014 | Timken et al. |
| 2014/0128654 A1 | 5/2014 | Fang et al. |
| 2014/0134065 A1 | 5/2014 | Timken et al. |
| 2014/0357915 A1* | 12/2014 | Lacheen .................. C07C 2/58 585/331 |

* cited by examiner

IONIC LIQUID REACTOR WITH HEAT EXCHANGER

RELATED APPLICATIONS

This application claims priority to U.S. Provisional Patent Application No. 62/090,970 filed on Dec. 12, 2014, the entirety of which is incorporated herein by reference.

FIELD OF THE INVENTION

This invention relates generally to an ionic liquid reactor and more particularly to an ionic liquid reactor with a heat exchanger.

BACKGROUND OF THE INVENTION

Ionic liquids are essentially salts in a liquid state, and are described in U.S. Pat. No. 4,764,440, U.S. Pat. No. 5,104,840, and U.S. Pat. No. 5,824,832. The properties vary extensively for different ionic liquids, and the use of ionic liquids depends on the properties of a given ionic liquid. Depending on the organic cation of the ionic liquid and the anion, the ionic liquid can have very different properties. The behavior of the ionic liquid varies considerably for different temperature ranges, and it is preferred to find ionic liquids that do not require operation under more extreme conditions such as refrigeration.

Acidic ionic liquid may be used as a catalyst in various chemical reactions, such as for the alkylation of iso-butane with olefins. The alkylation reaction is highly exothermic. To control the temperature, it is common for part of the unreacted light hydrocarbons to be vaporized. However, controlling the temperature by vaporization is undesirable because it makes the reactor operation, the ionic liquid dispersion, and the acid concentration more difficult to control. Therefore, it is believed to be more desirable to control the temperature while the reactants and products are maintained in liquid form.

While it would be desirable to utilize heat exchange to control the temperature, any heat exchanger will need to be configured to minimize the impact of the ionic liquid phase on heat transfer due to its high viscosity and potential for fouling of the heat transfer surface.

Additionally, as will be appreciated, conjunct polymer is often a byproduct of the various ionic liquid catalyst reactions including but not limited to alkylation, oligomerization, isomerization, and disproportionation. Conjunct polymer is typically highly conjugated, olefinic, highly cyclic hydrocarbons. The conjunct polymer is often associated with ionic liquid and will also impact heat transfer in similar ways as ionic liquid.

It would be desirable to provide an ionic liquid reactor that can effectively control the heat produced by exothermic reactions without the need of vaporization. It would also be desirable for such a reactor to account for the presence of conjunct polymer and ionic liquid catalyst.

SUMMARY OF THE INVENTION

An ionic liquid catalyst reactor and a process for controlling the heat of an ionic liquid catalyst reaction have been invented. The ionic liquid catalyst reactor and process utilize at least one external heat exchanger to remove the heat produced by the exothermic reactions. The various heat exchangers are designed to accommodate the hydrocarbons as well as the ionic liquid catalyst and the conjunct polymer that have a tendency to foul the equipment.

In a first aspect of the present invention, the invention may be broadly characterized as providing an ionic liquid catalyst reactor unit comprising: a first reaction zone having an inlet for ionic liquid, an inlet for a hydrocarbon stream, and an outlet for an effluent stream; a separation zone configured to receive the effluent stream and separate the effluent stream into a hydrocarbon phase and an ionic liquid phase; and, a first heat exchange zone configured to receive at least a portion of the effluent stream from the first reaction zone. The first heat exchange zone comprises an outlet for a cooled effluent stream, and an outlet for ionic liquid.

In various embodiments of the present invention, the first heat exchange zone comprises a heat exchanger with a shell and wherein the separation zone is disposed within the shell. It is contemplated that the shell includes an inlet for the effluent stream disposed below the outlet for the cooled effluent stream.

In some embodiments of the present invention, the first heat exchange zone comprises a heat exchanger comprising a shell and at least one baffle in the shell. It is contemplated that the at least one baffle comprises a baffle selected from the group consisting of: a helical baffle; a rod baffle; a grid baffle; an expanded metal baffle; and, a segmental baffle. It is also contemplated that the heat exchanger is configured to receive the effluent stream in a direction countercurrent to a direction of cooling fluid through the heat exchanger.

In various embodiments of the present invention, the first heat exchange zone comprises a spiral plate heat exchanger having a first flow path configured to receive the effluent stream and a second flow path configured to receive a cooling fluid. It is contemplated that the spiral plate heat exchanger comprises a collection pan and at least one flow path includes one or more openings to allow ionic liquid to drain from the at least one flow path to the collection pan.

In one or more embodiments of the present invention, the first heat exchange zone comprises at least one hair pin heat exchanger. It is contemplated that the at least one hair pin heat exchanger includes a boot configured to allow ionic liquid to be drained from the at least one hair pin heat exchanger.

In some embodiments of the present invention, the first heat exchange zone comprises at least one tube-in-shell heat exchanger having a horizontal orientation and comprising tubes inside of a shell with an inlet for an effluent stream on a top of the shell, and an outlet for a cooled effluent stream on a bottom of the shell. It is contemplated that the shell further comprises a boot configured to allow ionic liquid to be drained from the at least one tube-in-shell heat exchanger. It is further contemplated that the at least one tube-in-shell heat exchanger further comprises at least one grid baffle disposed within the shell.

In many embodiments of the present invention, the ionic liquid catalyst reactor unit further comprises: a second reaction zone having an inlet for ionic liquid, an inlet for a hydrocarbon stream, and an outlet for an effluent stream; and, a second heat exchange zone configured to receive at least a portion of the effluent stream from the second reaction zone and comprising an outlet for a cooled effluent stream and an outlet for ionic liquid. The first heat exchange zone may be disposed between the first reaction zone and the second reaction.

In at least one embodiment of the present invention, the ionic liquid catalyst reactor unit further comprises a plurality of reaction zone each having an inlet for ionic liquid, an inlet for a hydrocarbon stream, and an outlet for an effluent stream, the reaction zones arranged in series and, a plurality of heat exchange zones. It is preferred that at least one heat exchange zone is disposed between successive reaction zones.

In a second aspect of the present invention, the invention may be broadly characterized as providing process for controlling the temperature of a reaction performed in the presence of an ionic liquid catalyst by: performing a reaction in the presence of an ionic liquid catalyst to form an effluent, wherein the reaction is performed in a reaction zone; removing heat from at least a portion of the effluent from the reaction zone in a heat exchange zone with a cooling fluid to provide a cooled effluent; and, separating the effluent in a separation zone into a hydrocarbon phase and an ionic liquid phase.

In some embodiments of the present invention, the process include separating ionic liquid from the effluent from the reaction zone within the heat exchange zone. It is contemplated that the process includes passing the ionic liquid separated from the effluent in the heat exchange zone to a second reaction zone. It is further contemplated that the process also includes performing a reaction in the presence of an ionic liquid catalyst to form a second effluent, wherein the reaction is performed in the second reaction zone, and, passing the second effluent from the second reaction zone to a second heat exchange zone. It is also contemplated that the process further includes separating ionic liquid from the second effluent in the second heat exchange zone, and removing heat from the second effluent from the second reaction zone in the second heat exchange zone with a cooling fluid to provide a second cooled effluent.

Additional aspects, embodiments, and details of the invention, which may be combined in any manner, are set forth in the following detailed description of the invention.

DETAILED DESCRIPTION OF THE DRAWINGS

In the drawings of the present invention, one or more embodiments are shown in which like numerals denote like elements, and in which.

DETAILED DESCRIPTION OF THE INVENTION

As mentioned above, an ionic liquid catalyst reactor and a process for controlling the heat of an ionic liquid catalyst reaction have been invented which utilize an external heat exchanger. The heat exchanger is designed to allow reactants and ionic liquid acid catalyst to be in liquid phase. A heat exchange fluid will absorb heat from the reactor effluent mixture. By controlling the temperature with the heat exchanger and, more importantly without vaporization of the reactants, products, or ionic liquid, it will be easier to control the reactor operation, ionic liquid dispersion and acid concentration.

With these general principles of the present invention in mind, one or more exemplary embodiments of the present invention will now be described with the understanding that the following is exemplary in nature and is not intended to be limiting.

Figure 1:
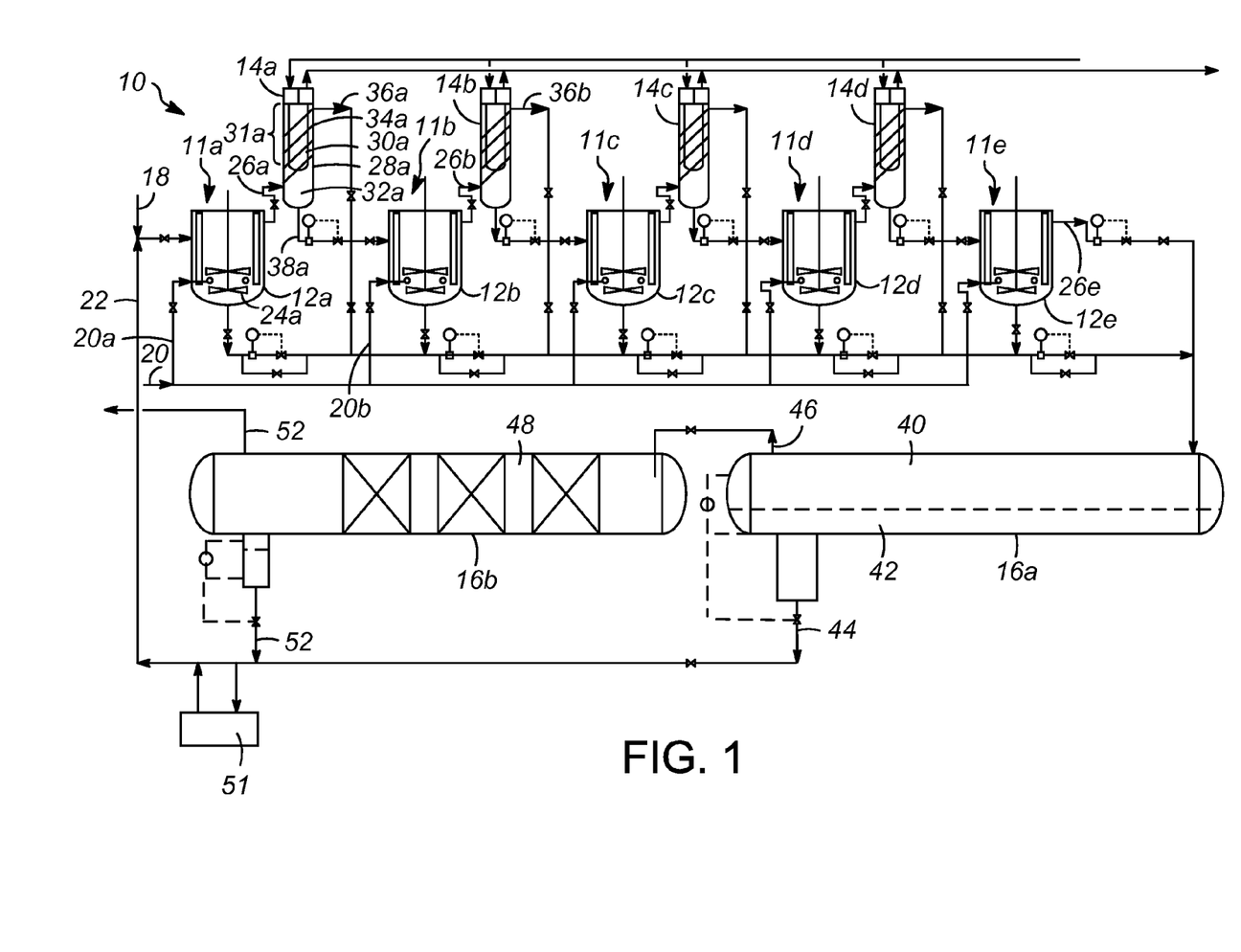
FIG. 1 shows an ionic liquid catalyst reactor unit according to one or more embodiments of the present invention with shell-and-tube heat exchangers in a vertical orientation and with helical baffles on the shell sides of the heat exchangers.

As shown in FIG. 1, a reactor unit 10 according to various embodiments of the present invention comprises at least one reaction zone 11a and at least one heat exchanger 14a. In addition to the at least one reaction zone 11a and the at least one heat exchanger 14a, the reactor unit 10 may further comprise at least one separation vessel 16a.

In a preferred embodiment, a plurality of reaction zones 11a, 11b, 11c, 11d, 11e are provided. For example, each of the reaction zones 11a, 11b, 11c, 11d, 11e may comprise a reactor vessel 12a, 12b, 12c, 12d, 12e, with the reactor vessels 12a, 12b, 12c, 12d, 12e being arranged in series. It should be appreciated that although not depicted as such, a single reactor vessel could be used with multiple separate reaction zones 11a, 11b, 11c, 11d, 11e contained within the single vessel. The at least one heat exchanger 14a is disposed between the reaction zone 11a and the at least one separation vessel 16a. Preferably, one heat exchanger 14a, 14b, 14c, 14d from a plurality of heat exchangers 14a, 14b, 14c, 14d is disposed between successive reaction zones 11a, 11b, 11c, 11d, 11e, as shown in FIG. 1.

In a preferred embodiment, the reactor unit 10 is utilized for an alkylation reaction, and therefore the present invention will be described in relation to an alkylation reaction, with the understanding that the present invention is not necessarily limited to same and can be practiced in association with different exothermic reactions.

As shown in FIG. 1, an $iC_4$ hydrocarbon stream 18 comprising $iC_4$ hydrocarbons is passed into the first reactor vessel 12a. An olefin hydrocarbon stream 20 comprising $C_4$ olefinic hydrocarbons is also passed into the first reactor vessel 12a. The olefinic hydrocarbon stream 20 can include $iC_4$ hydrocarbons as well to dilute the olefinic hydrocarbons before entering the reactor vessel 12a. The overall concentration of $iC_4$ hydrocarbons in the reactor vessel 12a is preferably well above the stoichiometric requirement of the alkylation reaction to minimize the side reactions of olefins with non-$iC_4$ hydrocarbons.

An ionic liquid catalyst stream 22 is also passed into the first reactor vessel 12a. As shown, the ionic liquid catalyst stream 22 is mixed with the $iC_4$ hydrocarbon stream 18 prior to being passed to the first reactor vessel 12a. This is merely preferred.

In the first reactor vessel 12a, which is operated under proper conditions, such as at a temperature of between 4.4° to 37.8° C. (40° to 100° F.) under a pressure that keeps all reactants and catalysts in liquid phase, the olefinic hydrocarbons will react with the $iC_4$ hydrocarbons to form alkylated hydrocarbons, primarily iso-octane and other trimethylpentanes. In order to mix the ionic liquid catalyst and the hydrocarbons, the first reactor vessel 12a includes an impeller 24a. The impeller 24a may also disperse the ionic liquid catalyst. The products of the reaction, as well as excess reactants (mainly iC$_4$ hydrocarbons) and the ionic liquid catalyst are passed out of the first reactor vessel 12a in an effluent stream 26a.

The effluent stream 26a from the first reactor vessel 12a is passed to the first heat exchanger 14a. As shown in FIG. 1, the heat exchanger 14a comprises a shell 28a with multiple U-shaped tubes 30a within the shell 28a. The U-shaped tubes 30a contain a heat exchange fluid, such as water or a refrigerant. As shown, the heat exchanger 14a in FIG. 1 has a vertical orientation (i.e., a longitudinal axis of the heat exchanger 14a is generally vertical).

The effluent stream 26a from the first reactor vessel 12a is preferably passed into the heat exchanger 14a into a lower or bottom portion that comprises a separation zone 32a. The separation zone 32a allows the heavier ionic liquid catalyst phase to separate from the effluent and accumulate on the bottom (due to the larger specific gravity compared to the hydrocarbons). The remaining components of the effluent will flow upwards in the shell 28a and contact the U-shaped tubes 30a with cooling fluid flowing through the tube side.

As will be appreciated, the cooling fluid in the U-shaped tubes 30a will absorb heat from the effluent in a heat exchange zone 31a of the heat exchanger 14a. In this embodiment, the separation zone 32a and the heat exchange zone 31a are contained within the shell 28a, or housing, of the heat exchanger 14a. It is also contemplated, but not shown that the separation zone 32a is within a separate vessel so as to allow for separation of the ionic liquid phase and the hydrocarbon phase prior to the effluent (or at least a portion thereof) passing into the heat exchange zone 31a.

Returning to FIG. 1, the heat exchanger 14a also includes baffles that may support the tubes and/or direct flow to improve heat transfer. A preferred baffle type is a helical baffle 34a. Any ionic liquid, or conjunct polymer, which separates from the effluent above the separation zone 32a may flow downward along the helical baffle 34a to the bottom of the heat exchanger 14a. In addition, the helical baffle 34a also streamlines the flow of fluid and reduces the creation of any stagnant zones in the heat exchanger 14a at the baffle (which would create accumulation of materials and restrict flow and heat exchange). Thus, while as would be appreciated other baffle types may be considered, the preferred helical baffle 34a minimizes the fouling tendency of ionic liquid and conjunct polymer passing through heat exchanger 14a and the negative impact on heat transfer from same.

A portion of a cooled effluent stream 36a may be passed from the heat exchanger 14a to the separator vessel 16a. A second portion of the cooled effluent stream 36a may be passed to the second reactor vessel 12b. Additionally, an ionic liquid catalyst stream 38a from bottom of the heat exchanger 14a may also be passed to the second reactor vessel 12b, passed to the first separation vessel 16a, or a combination thereof.

The second reactor vessel 12b will receive iC$_4$ hydrocarbons (and other hydrocarbons) from the cooled effluent stream 36a, a second olefin hydrocarbon stream 20b comprising C$_4$ olefinic hydrocarbons, and a second ionic liquid stream, in this case, from the ionic liquid catalyst stream 38a from bottom of the heat exchanger 14a. The second reactor vessel 12b may also receive an ionic liquid stream that comprises ionic liquid that may have separated in the first reactor 12a. The second reactor vessel 12b preferably operates in the same manner and under similar conditions as the first reactor vessel 12a and, thus will likewise produce an effluent stream 26b containing more alkylate components than effluent stream 26a.

The effluent stream 26b from the second reactor vessel 12b will be passed to the second heat exchanger 14b, which will function similarly to the first heat exchanger 14a. A cooled effluent stream 36b from the second heat exchanger 14b may be passed to a third reactor vessel 12c, and so on and so forth. As shown in FIG. 1, at the last reactor vessel, reactor vessel 12e, an effluent stream 26e is shown as being passed to the first separation vessel 16a instead of a heat exchanger. Such a configuration is preferred because it will lower the cost associated with the reactor unit 10 by not requiring an additional heat exchanger. Additionally, the increased temperature in the separation vessels 16a and 16b provided by the effluent stream 26e from the last reactor will facilitate better separation between the ionic liquid catalyst phase and the hydrocarbon phase. However, it should still be appreciated, that a heat exchanger could be disposed between the last reactor vessel and the first separation vessel 16a. As would be appreciated, the numbers of reactor vessels and heat exchangers can be varied for increased operation flexibility and vary from the exemplary embodiment shown in FIG. 1.

In the first separation vessel 16a, a mixture comprised of the effluent streams from the reaction zones 11a, 11b, 11c, 11d, 11e and ionic liquid catalyst streams will separate into a lighter hydrocarbon phase 40 and a heavier, ionic liquid catalyst phase 42. Preferably, in the first separation vessel 16a, at least 50%, and more preferably at least 90% of the ionic liquid catalyst will be separated from the hydrocarbons due to the different densities of the phases. The ionic liquid catalyst phase 42 can be withdrawn in an ionic liquid catalyst stream 44, which can be reused in the process, which can be regenerated, which can be disposed of, or a combination thereof. The hydrocarbon phase 40 can be withdrawn in a hydrocarbon effluent stream 46 which may be passed to a second separation vessel 16b.

In the second separation vessel 16b, entrained droplets of ionic liquid catalyst within the hydrocarbon phase 40 from the first separation vessel 16a may be further separated, for example with a coalescer material 48, such as glass beads, fibers or electrostatic separation devices. A second ionic liquid catalyst stream 50 (the numeral "52" near bottom of FIG. 1 should be changed to "50") comprising ionic liquid catalyst separated in the second separation vessel 16b can be combined with the ionic liquid catalyst stream 44. A hydrocarbon product stream 52, in this case comprising an alkylate product, can be passed from the second separation vessel 16b to a fractionation column (not shown) or other separation unit to separate the various hydrocarbons in the product stream 52. In various embodiments, the amount of ionic liquid in the hydrocarbon product stream 52 is preferably less than 100 ppm, and more preferably less than 20 ppm.

Figure 2:
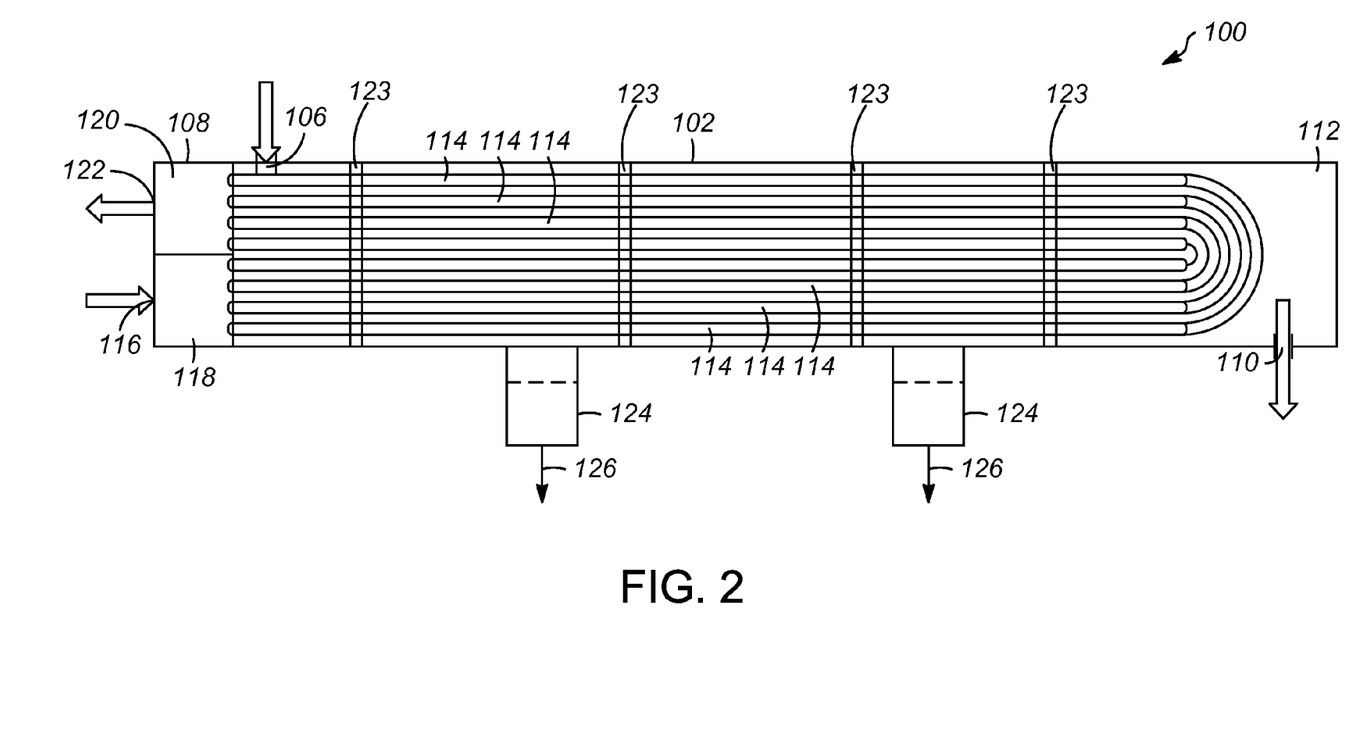
FIG. 2 shows a side cutaway view of a shell-and-tube heat exchanger that is in a horizontal orientation and may be used in one or more embodiments according to the present invention.

In another heat exchanger 100, shown in FIG. 2, the cooling fluid and the reactor effluent, for example the reactor effluent 26a shown in FIG. 1, preferably flow at least partially in a countercurrent manner to increase the cooling function of the cooling fluid.

In the embodiment shown, the heat exchanger 100 comprises a shell 102 with an inlet 106 proximate a first end 108 of the shell 102 and an outlet 110 proximate a second end 112 of the shell 102. A plurality of U-shaped tubes 114 extend from one end of the shell 102, preferably the first end 108, towards the second end 112 of the shell 102. The U-shaped tubes 114 will receive cooling fluid, which can pass from a cooling fluid inlet 116 to an inlet manifold 118 which will distribute the cooling fluid to the tubes 114. The heated cooling fluid may flow to an outlet manifold 120 and then be withdrawn through an outlet 122 and used elsewhere if desired. The hydrocarbons and ionic liquid will pass from the inlet 106 of the shell 102 to the outlet 110 of the shell 102, with the flow path between the inlet 106 and the outlet 110 being partially counter-current to the flow of cooling fluid through the tubes 114. Straight tubes extending from the first end 108 of the shell 102 to the second end 112 can also be used in the heat exchanger 100. The heat exchanger may include one or more baffles 123.

Figure 3:
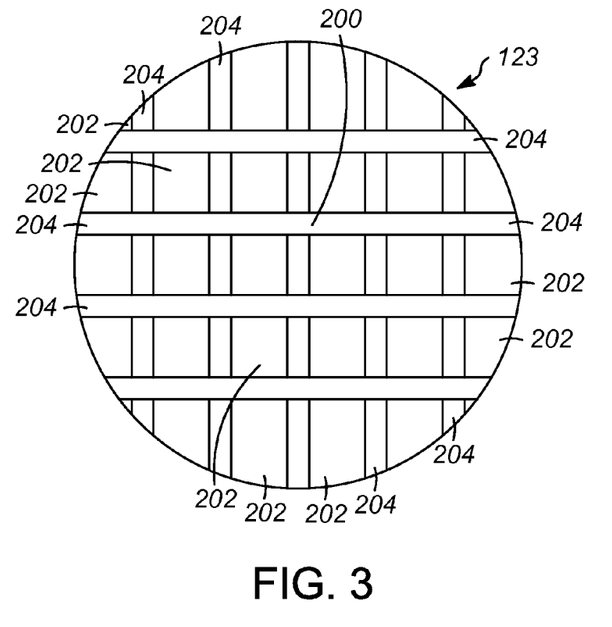
FIG. 3 shows a front view of a plurality of rod baffles arranged to form a grid used in the heat exchanger shown in FIG. 2.

For example, a plurality baffles 123 may be disposed within the shell 102 between the inlet 106 and the outlet 110. As shown in FIG. 3, the baffles 123 may comprise a plurality of rods 204 arranged to form a grid baffle 200 with a plurality of openings 202 for the fluids to flow there through and for the tubes 114 to extend there through. The rods 204 may be horizontal, vertical, or angular. As will be appreciated, the rods 204 need not be extended cylindrical members, but can be strips of material, dimpled sheets, or other shaped members. Additionally, the rods 204 can be configured in other designs and arrangements, such as alternating horizontal and vertical rods as shown in U.S. Pat. No. 5,139,084. Additionally, instead of rods 204, the baffles 123 may comprise alternating segmental baffles, such as shown in U.S. Pat. No. 4,699,211.

Returning to FIG. 2, the shell 102 of the heat exchanger 100 may also include a boot 124 to allow any ionic liquid that separates out to accumulate and be withdrawn from the heat exchanger 100 via an outlet 126. Multiple boots 124 or one boot 124 connecting multiple draining nozzles along the bottom of the heat exchanger 100 can be used. As shown, the heat exchanger 100 has a horizontal orientation, but an angular orientation could also be used.

Figure 4:
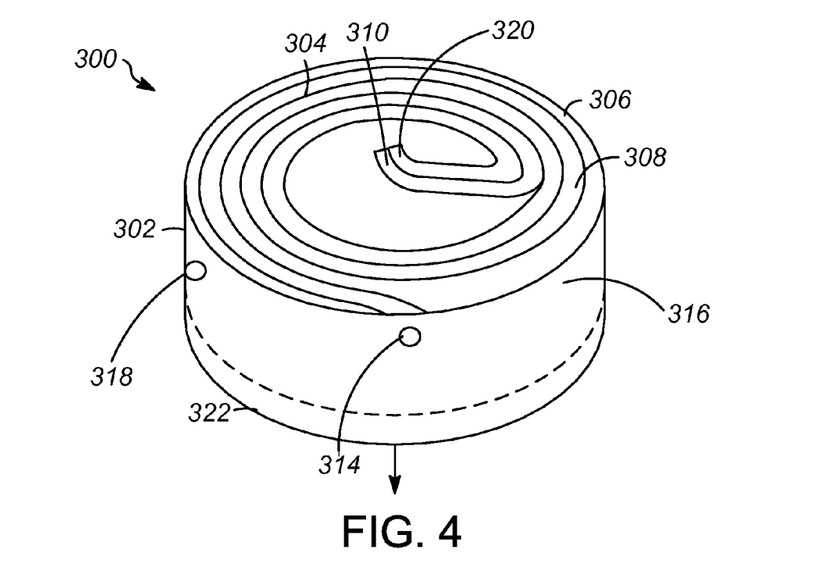
FIG. 4 shows an elevated side and top partially cutaway view of a spiral plate heat exchanger that may be used in one or more embodiments according to the present invention.
Figure 5:
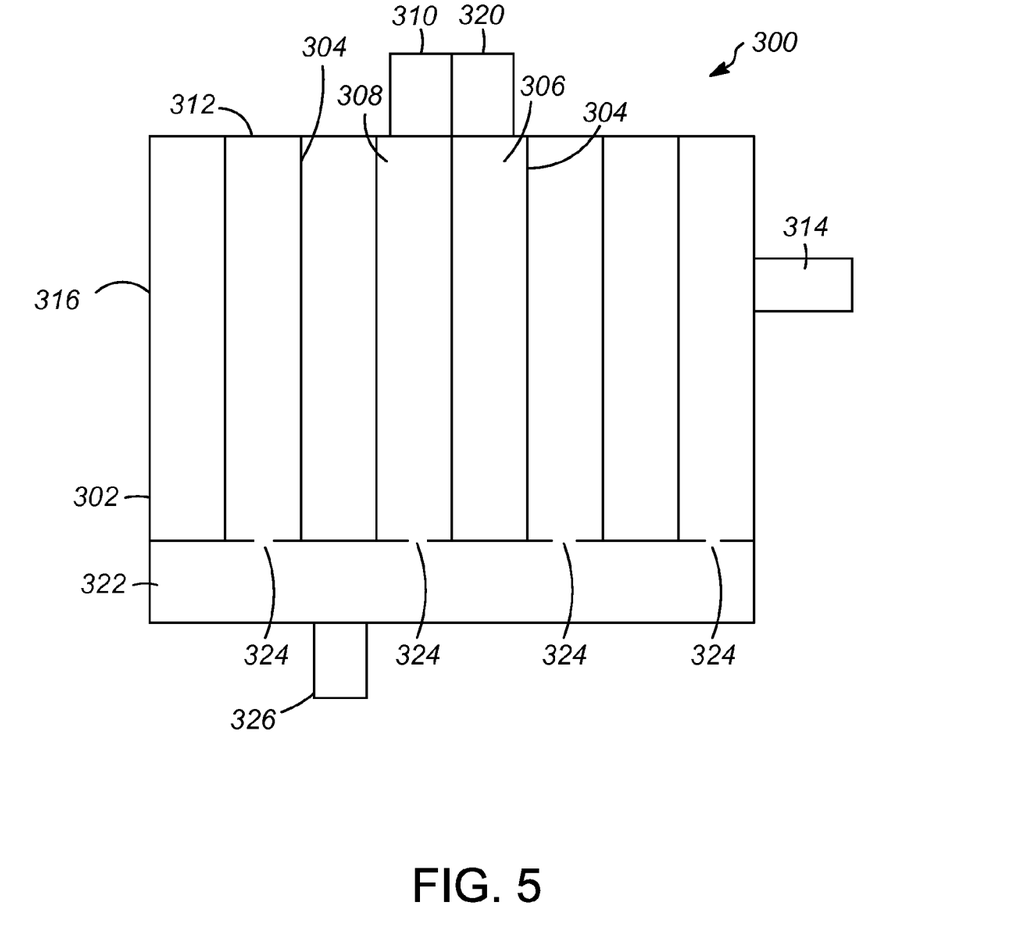
FIG. 5 shows a side cutaway view of the heat exchanger of FIG. 4.

Turning to FIGS. 4 and 5, another heat exchanger is shown which is contemplated to be used for the reactor and processes of the present invention in which the heat exchanger comprises a spiral plate heat exchanger 300. The spiral plate heat exchanger 300 includes a housing 302, or shell, and at least one plate channel 304 inside of the housing 302 that provides two spiral flow paths 306, 308. The first flow path 308 includes an inlet 310 preferably on a top 312 of the housing 302 and an outlet 314, preferably on a side surface 316 of the housing 302. The second flow path 306 includes an inlet 318, preferably on the side surface 316 of the housing 302, and an outlet 320, preferably on the top 312 of the housing 302. As will be appreciated, the references to "top" and "side" are in relation to the orientation shown in the Figures. Any change in the orientation of the heat exchanger 300 may result in the "top" being the "side."

In any orientation, the flow paths 306, 308 are preferably countercurrent in order to maximize the temperature difference between the two streams and increase the heat exchange, and thus the cooling, of the effluent stream. It is preferred that the inlet 318 for the second flow path 306 and the outlet 314 for the first flow path 308 are disposed 90 degrees apart along the side surface 316 of the heat exchanger 300.

As can be seen in FIG. 5, the heat exchanger 300 also includes a collection pan 322 for ionic liquid catalyst that can be used to collect the ionic liquid that separates from the effluent in the heat exchanger 300.

More specifically, the ionic liquid will be separated from the hydrocarbons along one of the flow paths 306, 308 containing ionic liquid and hydrocarbons inside the heat exchanger 300 as a result of the density difference between ionic liquid and the hydrocarbon. Additionally, centrifugal flow through the flow paths 306, 308 will accelerate the ionic liquid separation. In this case a separation zone and a heat exchange zone will both be contained within the housing 302 of the heat exchanger 300.

The settled ionic liquid at the bottom of one of flow paths 306, 308 can be drained into the collection pan 322 via one or more openings 324. In order to minimize the amount of the hydrocarbon phase that may pass through the openings, it is preferred that the openings are sized and disposed such that less than 10% of the total hydrocarbons, and preferably less than 5% of the total hydrocarbons, passes there through. The ionic liquid is preferably drained through a bottom boot 326 as, for example the ionic liquid catalyst stream 38a as shown in FIG. 1. It is also contemplated that the heat exchanger 300 includes individual drains on one or more revolutions of one of the spiral flow paths 306, 308 where the ionic liquid could be drained. These individual drains can be connected to valves or a boot or a separate vessel for removing ionic liquid.

The ionic liquid withdrawal rate from the separation zones and/or the ionic liquid level in the separation zones such as the bottom of heat exchangers in FIG. 1, the boots in FIG. 2 and the pan in FIG. 5 can be controlled to minimize the hydrocarbon entrainment in the ionic liquid.

Since some of the more viscous and heavier ionic liquid and conjunct polymer is separated from the reactor effluent before or within the heat exchangers, the heat transfer is improved and pressure drop reduced along the flow path due to less ionic liquid and conjunct polymer being present in the heat exchange zone and contacting the heat exchange surface (i.e., the spiral plate 304).

It is contemplated alternatively that the heat exchanger 300 with the spiral plate 304 is rotated 90 degrees (about the horizon) so that the flow of fluids is in a vertical direction (as opposed to a horizontal direction). In this case, the ionic liquid will not be separated from hydrocarbon in the spiral plate heat exchanger 300 and instead can be passed along to a sequential reactor or to a separation vessel or other equipment.

Figure 6:
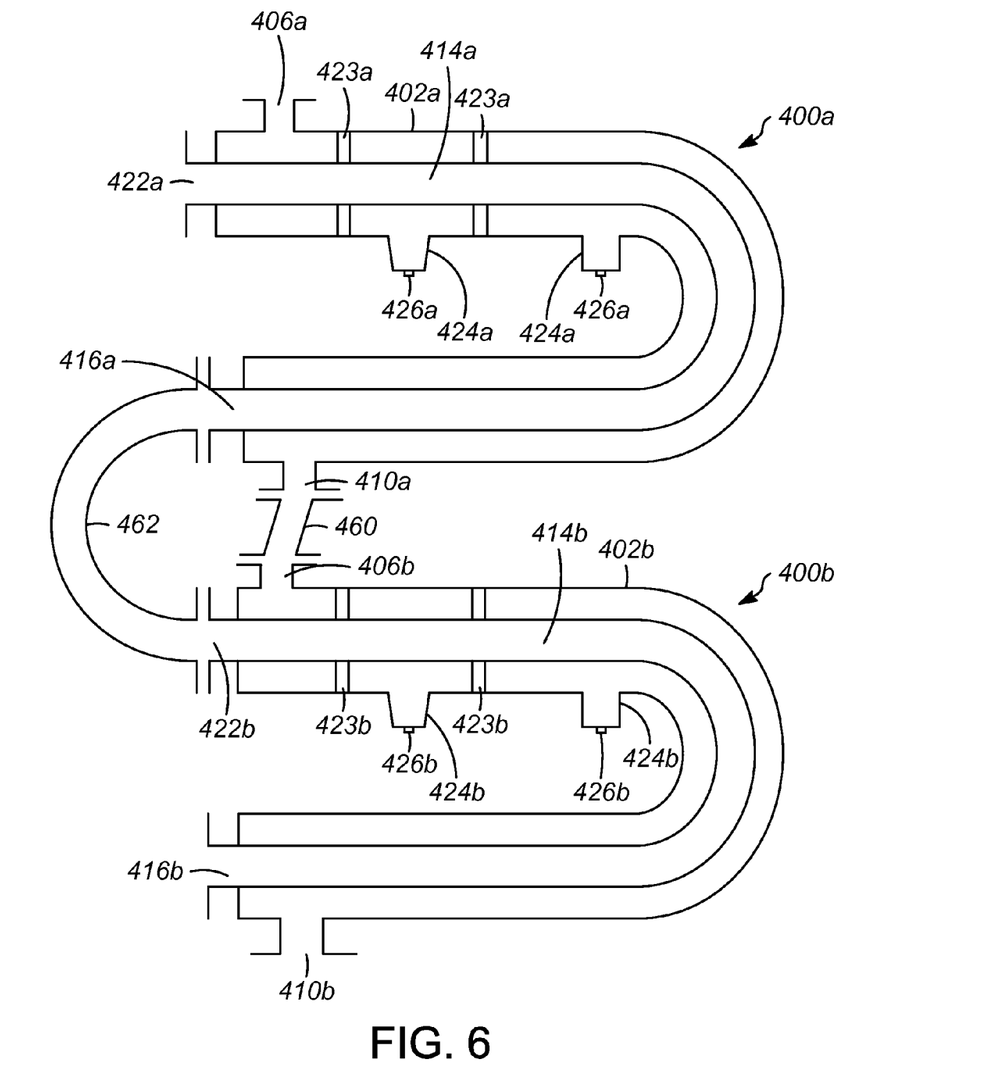
FIG. 6 shows a side cutaway view of two hairpin heat exchangers that may be used in one or more embodiments according to the present invention.

Another possible heat exchange configuration that may be utilized in accordance with the present invention is shown in FIG. 6. In FIG. 6, two hairpin heat exchangers 400a, 400b, are arranged in series. Although two hairpin heat exchangers 400a, 400b are shown, any number may be used, for example, one, more than one, two, etc.

With reference to the first hairpin heat exchange 400a, the hairpin heat exchange 400a includes a shell 402a with an inlet 406a and an outlet 410a. Extending within the shell 402a is at least one tube 414a also having an inlet 416a and an outlet 422a. As will be appreciated, the hairpin heat exchange 400a is designed so that the flow on the tube side is countercurrent to the flow on the shell side. Thus, the inlet 406a for the shell 402a and the outlet 422a for the tube 414a are disposed proximate the same end of the hairpin heat exchange 400a. If the flow on the tube side and the flow on the shell side was co-current, the inlet 422a for the shell 402a and the inlet 416a on the tube 414a would be disposed proximate each other on the same end of the hairpin heat exchange 400a. The remaining disclosure will utilize a preferred countercurrent flow, as it maximize the temperature differences between the hot and the cold fluids, with the understanding that a co-current flow could be utilized. Furthermore, in a preferred embodiment, reactor effluent (for example the reactor effluent 26a, FIG. 1) flows on the shell side and the cooling fluid flows on the tube side of the hairpin heat exchange 400a. Again, this configuration is merely preferred. The heat exchanger 400a also may include one or more baffles 423a. The baffles 423a may comprise one or more helical baffles, rod baffles, segmental baffles, or any other baffles. Finally, while the heat exchanger 400*a* is shown having a horizontal orientation, it is contemplated that a vertical or an angular orientation could also be used.

In use, the reactor effluent may pass through the inlet 406*a* of the shell 402*a* and flow towards the outlet 410*a* of the shell 402*a*. Ionic liquid may separate from the reactor effluent and can accumulate in one or more boots 424*a* disposed on the shell 402*a*. Any ionic liquid that separates out may be withdrawn from the heat exchanger 400*a* via an outlet 426*a*. Multiple boots 424*a* or one boot 424*a* connecting multiple draining nozzles along the bottom of the heat exchanger 400*a* can also be used. As shown preferably only the upper longitudinal portion of the heat exchanger 400*a* includes boots 424*a* for removing ionic liquid. The exact location and number of boots 424*a*, including none, can vary. Cooling fluid may pass through the inlet 416*a* of the tube 414*a* and flow towards the outlet 422*a*. As it passes through the tube 414*a*, it will absorb heat from the reactor effluent.

While only one heat exchanger 400*a* may be used, as shown in FIG. 6 a second heat exchanger 400*b* is shown in series. The second heat exchanger 400*b* may be the same or similar to the first heat exchanger 400*b* and thus the same components have similar reference numerals except for the "b" for the components of the second heat exchanger 400*b*. Furthermore, it is contemplated that the second heat exchanger 400*b* not include any boots. As shown a first conduit 460, such as a pipe or hose, connects the outlet 410*a* of the shell 402*a* of the first heat exchanger 400*a* to the inlet 406*b* of the shell 402*b* of the second heat exchanger 400*b*. Similarly, a second conduit 462 connects the outlet 422*b* of the tube 414*b* of the second heat exchanger 400*b* to the inlet 416*a* of the tube 414*a* of the first heat exchanger 400*a*. Thus, the cooling fluid will flow from the second heat exchanger 400*b* to the first heat exchanger 400*a*, while the reactor effluent will flow from the first heat exchanger 400*a* to the second heat exchanger 400*b*.

It is preferred to remove ionic liquid at locations close to the effluent inlet in the first heat exchanger so that the impact of ionic liquid and the associated conjunct polymer on the heat transfer downstream can be minimized. Additional withdrawal of ionic liquid along the flow path of the reactor effluent is optional.

With any of the various heat exchangers disclosed herein, it is believed that the fouling of the heat exchanger by the ionic liquid and conjunct polymer will be minimized through the separation of ionic liquid from reactor effluent, allowing the heat exchanger to remain effective for controlling the temperature of the reactor effluent.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An ionic liquid catalyst reactor unit comprising:
   a first reaction zone having an inlet for ionic liquid, an inlet for a hydrocarbon stream, and an outlet for an effluent stream;
   a separation zone configured to receive the effluent stream and separate the effluent stream into a hydrocarbon phase and an ionic liquid phase; and,
   a first heat exchange zone configured to receive at least a portion of the effluent stream from the first reaction zone and comprising:
   an outlet for a cooled effluent stream, and an outlet for ionic liquid wherein the first heat exchange zone comprises a heat exchanger with a shell and wherein the separation zone is disposed within the shell.

2. The ionic liquid catalyst reactor unit of claim 1 wherein the shell includes an inlet for the effluent stream disposed below the outlet for the cooled effluent stream.

3. The ionic liquid catalyst reactor unit of claim 1, wherein the first heat exchange zone comprises a heat exchanger comprising a shell and at least one baffle in the shell.

4. The ionic liquid catalyst reactor unit of claim 3 wherein the at least one baffle comprises a baffle selected from the group consisting of: a helical baffle; a rod baffle; a grid baffle; an expanded metal baffle; and, a segmental baffle.

5. The ionic liquid catalyst reactor unit of claim 3 wherein the heat exchanger is configured to receive the effluent stream in a direction countercurrent to a direction of cooling fluid through the heat exchanger.

6. The ionic liquid catalyst reactor unit of claim 1, wherein the first heat exchange zone comprises a spiral plate heat exchanger having a first flow path configured to receive the effluent stream and a second flow path configured to receive a cooling fluid.

7. The ionic liquid catalyst reactor unit of claim 6, wherein the spiral plate heat exchanger comprises a collection pan and at least one flow path includes one or more openings to allow ionic liquid to drain from the at least one flow path to the collection pan.

8. The ionic liquid catalyst reactor unit of claim 1 wherein the first heat exchange zone comprises at least one hair pin heat exchanger.

9. The ionic liquid catalyst reactor unit of claim 8 wherein the at least one hair pin heat exchanger includes a boot configured to allow ionic liquid to be drained from the at least one hair pin heat exchanger.

10. The ionic liquid catalyst reactor unit of claim 1 wherein first heat exchange zone comprises at least one tube-in-shell heat exchanger having a horizontal orientation and comprising tubes inside of a shell with an inlet for an effluent stream on a top of the shell, and an outlet for a cooled effluent stream on a bottom of the shell.

11. The ionic liquid catalyst reactor unit of claim 10 wherein the shell further comprises a boot configured to allow ionic liquid to be drained from the at least one tube-in-shell heat exchanger.

12. The ionic liquid catalyst reactor unit of claim 10 wherein the at least one tube-in-shell heat exchanger further comprises at least one grid baffle disposed within the shell.

13. The ionic liquid catalyst reactor unit of claim 1 further comprising:

a second reaction zone having an inlet for ionic liquid, an inlet for a hydrocarbon stream, and an outlet for an effluent stream;

a second heat exchange zone configured to receive at least a portion of the effluent stream from the second reaction zone and comprising an outlet for a cooled effluent stream and an outlet for ionic liquid, and wherein the first heat exchange zone is disposed between the first reaction zone and the second reaction.

14. The ionic liquid catalyst reactor unit of claim 1 further comprising:

a plurality of reaction zone each having an inlet for ionic liquid, an inlet for a hydrocarbon stream, and an outlet for an effluent stream, the reaction zones arranged in series; and, a plurality of heat exchange zones, at least one heat exchange zone being disposed between successive reaction zones.

15. A process for controlling the temperature of a reaction performed in the presence of an ionic liquid catalyst, the process comprising:

performing a reaction in the presence of an ionic liquid catalyst to form an effluent, wherein the reaction is performed in a reaction zone;

removing heat from at least a portion of the effluent from the reaction zone in a heat exchange zone with a cooling fluid to provide a cooled effluent;

separating the effluent in a separation zone into a hydrocarbon phase and an ionic liquid phase and;

separating ionic liquid from the effluent from the reaction zone within the heat exchange zone.

16. The process of claim 15 further comprising:

passing the ionic liquid separated from the effluent in the heat exchange zone to a second reaction zone.

17. The process of claim 16 further comprising:

performing a reaction in the presence of an ionic liquid catalyst to form a second effluent, wherein the reaction is performed in the second reaction zone; and, passing the second effluent from the second reaction zone to a second heat exchange zone.

18. The process of claim 15 further comprising:

separating ionic liquid from the second effluent in the second heat exchange zone; and, removing heat from the second effluent from the second reaction zone in the second heat exchange zone with a cooling fluid to provide a second cooled effluent.

* * * * *